US012724022B2

(12) United States Patent
Sharma et al.

(10) Patent No.: US 12,724,022 B2
(45) Date of Patent: Sep. 1, 2026

(54) PROCESSES AND SYSTEMS FOR MONITORING ONE OR MORE GASES DISSOLVED IN A LIQUID

(71) Applicant: Schlumberger Technology Corporation, Sugar Land, TX (US)

(72) Inventors: Richa Sharma, Cambridge, MA (US); Quincy K. Elias, Cambridge, MA (US); Terizhandur S. Ramakrishnan, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 396 days.

(21) Appl. No.: 18/553,018

(22) PCT Filed: Mar. 29, 2022

(86) PCT No.: PCT/US2022/022306
§ 371 (c)(1),
(2) Date: Sep. 28, 2023

(87) PCT Pub. No.: WO2022/212344
PCT Pub. Date: Oct. 6, 2022

(65) Prior Publication Data

US 2025/0076274 A1 Mar. 6, 2025

Related U.S. Application Data

(60) Provisional application No. 63/167,412, filed on Mar. 29, 2021.

(51) Int. Cl.
*G01N 33/28* (2006.01)
*G01J 3/02* (2006.01)
(Continued)

(52) U.S. Cl.
CPC ........ *G01N 33/2841* (2013.01); *G01J 3/0227* (2013.01); *G01J 3/18* (2013.01);
(Continued)

(58) Field of Classification Search
CPC .. G01N 33/2841; G01N 21/274; G01N 21/65; G01N 21/84; G01N 2021/8405;
(Continued)

(56) References Cited

U.S. PATENT DOCUMENTS 4,648,714 A 3/1987 Benner
5,525,008 A 6/1996 Wilson
(Continued)

FOREIGN PATENT DOCUMENTS

CN 107121425 A 9/2017

OTHER PUBLICATIONS

Asundi, R.K., et al., Fermi Resonance in Benzene, Nature, vol. 163, Apr. 23, 1949, 1 Page.
(Continued)

*Primary Examiner* — Francis C Gray
(74) *Attorney, Agent, or Firm* — Jeffrey D. Frantz

(57) ABSTRACT

Processes and systems for monitoring one or more gases dissolved in a liquid. In some embodiments, the process can include introducing a fluid into an inlet of a sample cell, where the fluid includes at least one gas dissolved in a liquid. The fluid can flow through the sample cell such that at least a portion of the fluid flows past an optical window such that the fluid is viewable within the sample cell through the optical window. The fluid can be recovered from an outlet of the sample cell. An electromagnetic radiation signal can be emitted into the sample cell through the optical window for at least a portion of the time the fluid is viewable through the optical window. The fluid can be contacted with the electromagnetic radiation signal within the sample cell. A scat-
(Continued)

tered electromagnetic radiation signal that can include elastic scattered radiation and inelastic scattered radiation emitted from the sample cell through the optical window can be directed into a filter to remove at least a portion of the elastic scattered radiation to produce a primarily inelastic scattered radiation signal. The primarily inelastic scatted radiation signal can be directed to a detector to detect a Raman signal indicating the presence of the at least one dissolved gas in the liquid.

28 Claims, 7 Drawing Sheets

(51) Int. Cl.
*G01J 3/18* (2006.01)
*G01J 3/28* (2006.01)
*G01J 3/44* (2006.01)
*G01N 21/27* (2006.01)
*G01N 21/65* (2006.01)
*G01N 21/84* (2006.01)

(52) U.S. Cl.
CPC ............... *G01J 3/2803* (2013.01); *G01J 3/44* (2013.01); *G01N 21/274* (2013.01); *G01N 21/65* (2013.01); *G01N 21/84* (2013.01); *G01J 2003/2813* (2013.01); *G01N 2021/8405* (2013.01)

(58) Field of Classification Search
CPC ............ G01N 21/0317; G01N 21/3577; G01J 3/0227; G01J 3/18; G01J 3/2803; G01J 3/44; G01J 2003/2813
See application file for complete search history.

(56) References Cited

U.S. PATENT DOCUMENTS

| | | | | |
|---|---|---|---|---|
| 9,500,583 | B2 | 11/2016 | Jiang | |
| 2008/0111064 | A1* | 5/2008 | Andrews | G01V 8/02 250/269.1 |
| 2009/0213369 | A1* | 8/2009 | Lee | B82Y 5/00 424/617 |
| 2014/0000881 | A1 | 1/2014 | Player | |
| 2014/0043607 | A1 | 2/2014 | Wang | |
| 2014/0245826 | A1* | 9/2014 | Pope | E21B 49/088 73/152.24 |
| 2019/0079007 | A1 | 3/2019 | Sharma | |
| 2020/0018162 | A1* | 1/2020 | Price | G01J 3/027 |
| 2025/0076274 | A1 | 3/2025 | Sharma | |

OTHER PUBLICATIONS

Bondor, P. L. et al., "Applications of Carbon Dioxide in Enhanced Oil Recovery", in Energy Conversion and Management, vol. 33, No. 5-8, , May 1, 1992, pp. 579-586.

Ho, K. L., et al., "An Ab Initio Anharmonic Approach to Study Vibrational Spectra of Small Ammonia Clusters", Electronic supplementary information, Oct. 6, 2016.

Holm et al., "Mechanisms of Oil Displacement by Carbon Dioxide", in Journal of Petroleum Technology, vol. 26, Issue 12, Dec. 1, 1974, pp. 1427-1438.

Martin, D., et al., "Carbon Dioxide Flooding", in Journal of Petroleum Technology, vol. 44, Issue 04, Apr. 1, 1992, pp. 396-400.

Martin, J. W. "Additional Oil Production through Flooding with Carbonated Water" Producers Monthly, Jul. 1951, pp. 18-22.

Orr, F. M., et al., "Use of Carbon Dioxide in Enhanced Oil Recovery", 3, in Science, vol. 224, Issue 4649, May 11, 1984, pp. 563-569.

Portier, S., et al., "Modelling CO2 Solubility in Pure Water and Nacl-Type Waters From 0 to 300° C. and From 1 to 300 Bar: Application to the Utsira Formation at Sleipner", in Chemical Geology, vol. 217, Issue 3, Apr. 25, 2005, pp. 187-199.

Ramachandran, C. N., et al., "Water Clustering in the Presence of a CO2 Molecule", in Computational and Theoretical Chemistry, vol. 966, Issue 1, Jun. 2011, pp. 84-90.

Hirofumi, S., et al., "Which Carbon Oxide Is More Soluble Ab Initio Study on Carbon Monoxide and Dioxide in Aqueous Solution", in Chemical Physics Letters, vol. 323, No. 3-4, Jun. 16, 2000, pp. 257-262.

Valerie, R.G., et al., Fermi Resonance in CO2: A Combined Electronic Coupled-Cluster and Vibrational Configuration-Interaction Prediction, The Journal of Chemical Physics, Mar. 23, 2007, pp. 1-6.

Nguyen, M. T.,et al., "How Many Water Molecules Are Actively Involved in the Neutral Hydration of Carbon Dioxide", in the Journal of Physical Chemistry A, vol. 101, Issue 40, Oct. 2, 1997, pp. 7379-7388.

Jiao, D., et al., "CO2 Solvation Free Energy Using Quasi-Chemical Theory", in the Journal of Chemical Physics, vol. 134, Issue 22, Jun. 14, 2011, pp. 1-9.

Duan, Z., et al., "An Improved Model Calculating CO2 Solubility in Pure Water and Aqueous Nacl Solutions From 273 to 533 K and From 0 to 2000 Bar", in Chemical Geology, vol. 193, Issue 3, Feb. 14, 2003, pp. 257-271.

Holm, L. W. "Carbon Dioxide Solvent Flooding for Increased Oil Recovery",Published in Petroleum Transactions, AIME, vol. 216, Issue 01, Dec. 1, 1959, pp. 225-231.

Blunt, M., et al., "Carbon Dioxide in Enhanced Oil Recovery", in Energy Conversion and Management, vol. 34, Issue 9, Sep. 1, 1993, pp. 1197-1204.

Dayanand, S., "CO2-Prophet Model Based Evaluation of CO2-EOR and Storage Potential in Mature Oil Reservoirs", in Journal of Petroleum Science and Engineering, vol. 134, Oct. 1, 2015, pp. 79-86.

* cited by examiner

PROCESSES AND SYSTEMS FOR MONITORING ONE OR MORE GASES DISSOLVED IN A LIQUID

CROSS-REFERENCE TO RELATED APPLICATIONS

This Application is a National Stage Entry of International Patent Application No. PCT/US2022/022306, filed on Mar. 29, 2022, which claims priority to U.S. Provisional Patent Application No. 63/167,412, filed on Mar. 29, 2021, the entirety of which is incorporated herein.

FIELD

Embodiments described generally relate to processes and systems for monitoring one or more gases dissolved in a liquid. More particularly, such embodiments relate to the use of Raman spectroscopy to monitor one or more gases, e.g., carbon dioxide ($CO_2$), dissolved in a liquid, e.g., water or hydrocarbon oil.

BACKGROUND

Accurate and continuous monitoring of dissolved gases, e.g., carbon dioxide, in a liquid, e.g., water or hydrocarbon oil, in high pressure conditions continues to be a challenge in many field applications, including carbon dioxide capture, storage, and enhanced oil recovery. Transmission infrared (IR) measurements have been used for the sensing of gaseous mixtures because of the relative ease and sensitivity in noninterfering mixtures. However, the accuracy of transmission IR measurement systems can be sensitive to scattering properties even under ideal measurement conditions and also overlap with water vapor. Transmission mid-IR measurements also require small path lengths at moderate gas pressure. Even for sensing dissolved gases in liquids transmission path lengths need to be below 100 μm. It is for this reason that attenuated total reflection (ATR) appears attractive, but it is beset with drawbacks arising from surface contamination.

With the exception of ATR at mid-IR, the majority of processes used to determine the presence of one or more dissolved gases in a liquid involves degassing a sample and analyzing the degassed gas phase. Degassing, however, is not an assured measurement process because the amount of gas in the liquid is not known. Additionally, the degassing approach also requires obtaining phase volumetric measurements.

There is need, therefore, for improved processes and systems for monitoring one or more gases, e.g., carbon dioxide, dissolved in a liquid, e.g., water or hydrocarbon oil.

SUMMARY

Processes and systems for monitoring one or more gases dissolved in a solvent are provided. In some embodiments, the process can include introducing a fluid into an inlet of a sample cell, where the fluid includes at least one gas dissolved in a liquid. The fluid can flow through the sample cell such that at least a portion of the fluid flows past an optical window such that the fluid is viewable within the sample cell through the optical window. The fluid can be recovered from an outlet of the sample cell. An electromagnetic radiation signal can be emitted into the sample cell through the optical window for at least a portion of the time the fluid is viewable through the optical window. The fluid can be contacted with the electromagnetic radiation signal within the sample cell. A scattered electromagnetic radiation signal that can include elastic scattered radiation and inelastic scattered radiation emitted from the sample cell through the optical window can be directed into a filter to remove at least a portion of the elastic scattered radiation to produce a primarily inelastic scattered radiation signal. The primarily inelastic scatted radiation signal can be directed to a detector to detect a Raman signal indicating the presence of the at least one dissolved gas in the liquid.

Processes for calibrating a Raman system are also provided. In some embodiments, the process for calibrating a Raman system can include preparing a mixture that can include water and at least one gas at a pressure of about 14.7 psi-absolute to about 2,000 psi-absolute. The at least one gas can be dissolved in the water. The mixture can be at thermodynamic equilibrium. The mixture can flow through a flowline and into an inlet of a sample cell. Degassing in the flowline can be substantially avoided by increasing the pressure by at least 1 psi-absolute above the pressure the mixture of water and the at least one gas was prepared. The mixture can flow through the sample cell. At least a portion of the mixture can flow past an optical window such that the mixture can be viewable within the sample cell through the optical window. The mixture can be recovered from an outlet of the sample cell. An electromagnetic radiation signal can be emitted into the sample cell through the optical window for at least a portion of the time the mixture is viewable through the optical window. The mixture can be contacted with the electromagnetic radiation signal within the sample cell. A scattered electromagnetic radiation signal that can include elastic scattered radiation and inelastic scattered radiation emitted from the sample cell can be directed through the optical window into a filter to remove at least a portion of the elastic scattered radiation to produce a primarily inelastic scattered radiation signal. The primarily inelastic scatted radiation signal can be directed to a detector to detect a Raman signal indicating the presence of the at least one gas dissolved in the liquid. The Raman signal can be correlated to a dissolved concentration of the at least one gas with a thermodynamic model for the mixture of water and the at least one gas.

DETAILED DESCRIPTION

Figure 1:
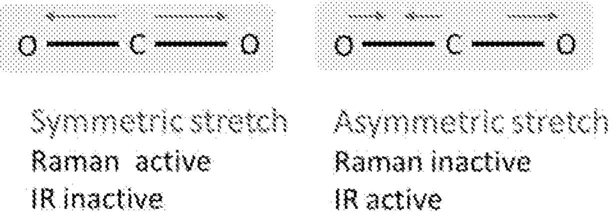
FIG. 1 illustrates mutual exclusion principles as seen in $CO_2$ for symmetric and asymmetric stretch.

It has been discovered that a Raman spectroscopy system can be used for quantitative inference of one or more gases, e.g., carbon dioxide, dissolved in a liquid, e.g., water and/or hydrocarbon oil. The identification of component(s) present in a given sample of the one or more gases dissolved in a liquid and the amount(s) thereof can be based, at least in part, on spectral peaks and magnitudes thereof. In some embodiments, the molar ratio(s) of two or more components present in the given sample of the gas(es) dissolved in the liquid can be based, at least in part, on the spectral peaks and magnitudes thereof.

In some embodiments, the Raman spectroscopy system can be used alone to identify components and molar ratios thereof in a given sample. In other embodiments, the Raman spectroscopy system can be used in addition to existing transmission IR measurements, e.g., transmission mid-IR measurements. Without wishing to be bound by theory, it is believed that when the Raman spectroscopy system is used in conjunction with an existing transmission IR measurement system that more accurate compositional determinations can be made.

In some embodiments, the processes and systems disclosed herein can be used to analyze separate samples of the gas(es) dissolved in the liquid. In other embodiments, the processes and systems disclosed herein can be used to continuously analyze for a predetermined period of time a flowing stream of interest that includes or can include one or more gases dissolved in a liquid, e.g., water or hydrocarbon oil. The gas(es) that can be detected with the Raman spectroscopy system can be or can include, but is not limited to, carbon dioxide, methane ($CH_4$), hydrogen sulfide ($H_2S$), or any mixture thereof.

The operational concept of the Raman spectroscopy is based on Raman scattering due to incident light photon interaction with electron clouds and bonds of a molecule. During the interaction, the vibrational energy of the molecule increases in Stokes scattering with a decrease in photon energy. The opposite occurs in anti-Stokes scattering.[1] Scattered light spectrum is a signature of the energy change and is associated with molecular polarizability and vibrational modes of the molecule. Since vibrational energy levels are known for the chemical bonds, the Raman spectrum essentially provides a "fingerprint" of the chemical bonds, and therefore the molecule. Fundamentally, the frequencies of these molecular vibrations depend on the structure of the molecule and its interaction with the environment. Accordingly, Raman spectral features can be used to probe not only the intermolecular interactions but also quantitatively estimate the concentration of gas(es) dissolved in the liquid, e.g., water or hydrocarbon oil, at both surface and downhole environments. For the downhole environments, the sample cell can be configured for relatively high-pressure measurements. Additionally, since IR spectroscopy is based on direct absorption of photons and Raman spectroscopy is based on inelastic scattering of photons, the two types of spectroscopy can usually be used together and can complement each other. In some embodiments, Raman spectroscopy can be used to sense or otherwise detect the presence of carbon dioxide ($CO_2$), methane ($CH_4$), hydrogen sulfide ($H_2S$), or any mixture thereof dissolved in a liquid, e.g., water or hydrocarbon oil. In some embodiments, the IR spectroscopy can be used to sense or otherwise detect the presence of $CO_2$, $CH_4$, $H_2S$, $N_2$, or any mixture thereof dissolved in the liquid.

Classical electromagnetic field (EM) theory can be used to explain many features of Raman spectral bands. As per EM theory $p=\alpha E$, where p is the induced dipole moment in a molecule due to an external electric field E, and the proportionality constant $\alpha$ is the electric polarizability of the molecule. For this explanation, the medium has been assumed to be isotropic. Electric polarizability is the relative tendency of the electron cloud of an atom or molecule to be distorted from its normal shape i.e., in the absence of an electric field. Raman scattering occurs when molecular vibration changes $\alpha$. The selection rule for a Raman-active vibration can be captured as the non-zero polarizability derivative $$\frac{\partial \alpha}{\partial Q} \neq 0,$$

where Q represents the vibration coordinate.

Raman and infrared (IR) selection rules are analogous to each other: the selection rule for IR-active vibration is the net change in permanent dipole moment during vibration $$\left(\frac{\partial \mu}{\partial Q} \neq 0\right),$$

and for Raman active it is the non-zero polarizability derivative $$\left(\frac{\partial \alpha}{\partial Q} \neq 0\right).$$

From group theory,[1,2] one can show that if a molecule has a center of symmetry, vibrations that are Raman active are IR inactive, and vice versa. This principle of mutual exclusion can be applied to a $CO_2$ molecule. More particularly, FIG. 1 illustrates the mutual exclusion principle as seen in $CO_2$ for symmetric and asymmetric stretch. Note that in the case of a complex molecule that has no symmetry (except the identity element), all the normal modes may be active in both IR and Raman.

In general, Raman and IR spectra are neither mutually exclusive nor duplicative. The different photon-molecule interaction results in different "line shapes" for Raman spectra from those of IR absorption, even when both are active. The advantages of Raman spectra are (i) the response is directly proportional to the (molar) density of the analyte molecules; (ii) O—H band of water does not overlap with the bands of other functional groups of interest in the oil field; and (iii) the bands of interest for oil-field sensing have minimum overlap with each other.

Figure 2:
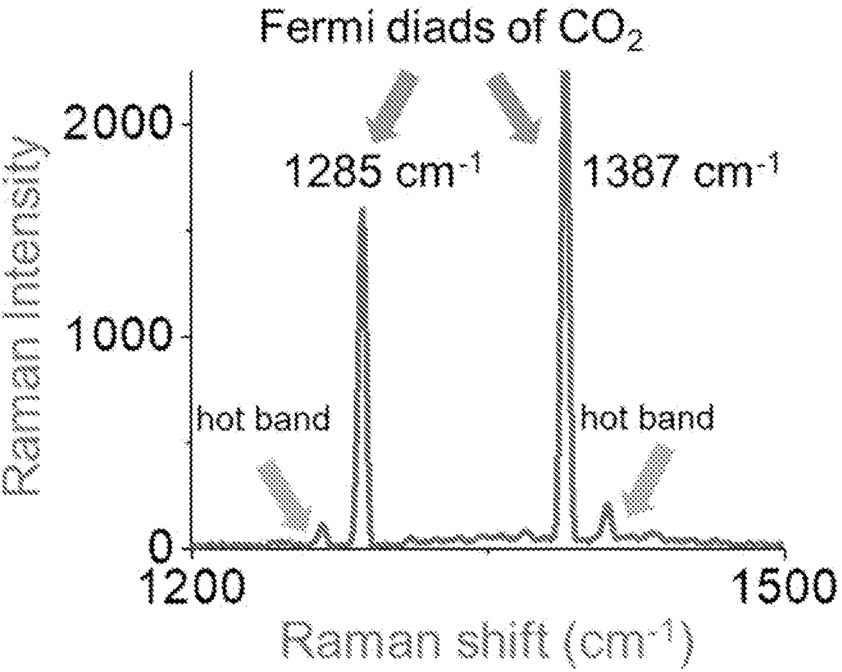
FIG. 2 depicts Raman spectra of $CO_2$ gas (99.8%) at 13.7 Bar and 22.2° C. acquired via measurement with an illustrative Raman cell disclosed herein, according to one or more embodiments described.

The Raman spectrum of most molecules typically have isolated vibrational coordinates resulting from their fundamental vibrations. In the case of a $CO_2$ molecule, the fundamental in-phase stretch and the first $CO_2$ bend overtone interact leading to a phenomenon called Fermi resonance.[1,3] Fermi resonance was also first discovered for the $CO_2$ molecule, and later seen for many molecules.[1, 3-5] The linear combination or mixing of the fundamental in-phase symmetric stretch ($\nu_1$) and the $CO_2$ bend overtone ($2\nu_2$) lead to Fermi resonance doublet observed at 1385 $cm^{-1}$ ($\nu_+$) and 1278 $cm^{-1}$ ($\nu_-$) (at 22.2° C.). See, e.g., references 1 and 3. The Raman spectrum of $CO_2$(g) in FIG. 2 shows the two strong peaks of Fermi resonance known as Fermi diads. The Raman spectrum in FIG. 2 shown in FIG. 2 was of pure $CO_2$ gas (99.8%) and was obtained in a high pressure Raman cell (described in more detail below) at a pressure of 13.7 Bar and at a temperature of 22.2° C. The two minor peaks of Fermi resonance are assigned to hot bands and are not useful for most sensing applications. Also, the two minor peaks of Fermi resonance are typically not observed in the solvated $CO_2$ spectrum.

Molecular clusters of $CO_2$-water ($CO_2$—$(H_2O)_n$) is an active area of research. Several quantum chemical studies[6-8] suggest a variety of different sized clusters of $CO_2$—$(H_2O)_n$ form where n is the number of $H_2O$ molecules. Depending on the number of $H_2O$ molecules in the cluster, the structure of the cluster is seen to change in these calculations.[8] In going from n=1 to n=6, the clusters can be $CO_2 \cdot H_2O$; $CO_2 \cdot (H_2O)_2$; $CO_2 \cdot (H_2O)_3$; $CO_2 \cdot (H_2O)+$; $CO_2 \cdot (H_2O)_5$; and $CO_2 \cdot (H_2O)_6$. See reference 8 for structures that were derived based on quantum mechanical calculations.

Figure 3:
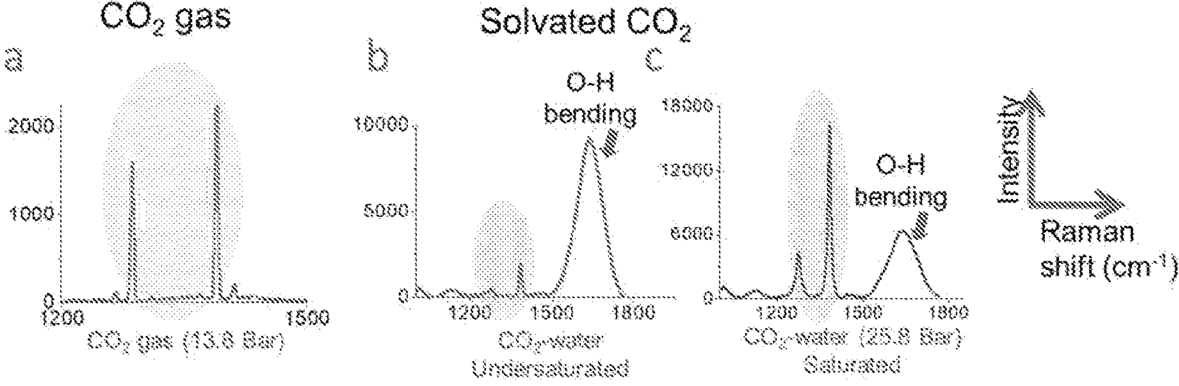
FIG. 3 depicts Raman spectra of $CO_2$ gas (99.8%) at 13.7 Bar and 22.2° C., of undersaturated $CO_2$ gas (99.8%) in water at 22.2° C., and saturated $CO_2$ gas (99.8%) in water at 25.8 Bar and 22.2° C. acquired via measurement with an illustrative Raman cell disclosed herein, according to one or more embodiments described.

The Raman signal of solvated $CO_2$ shown in FIG. 3 shows the distinct peaks of $CO_2$ and water molecules. The solvated or dissolved $CO_2$ in water has the Raman peaks or Fermi diads at (1275 $cm^{-1}$) and 1383 $cm^{-1}$ (FIG. 2). The Fermi diads of $CO_2$ are broader when dissolved in water than when in the gas phase. This peak broadening arises from the $CO_2$—$H_2O$ molecular interactions (see FIG. 4). It should be noted that the symmetry of $CO_2$ vibration resulting in Fermi diads is not broken by this weak intermolecular interaction and is available for monitoring the $CO_2$ molecule in the mixture.

Figure 4:
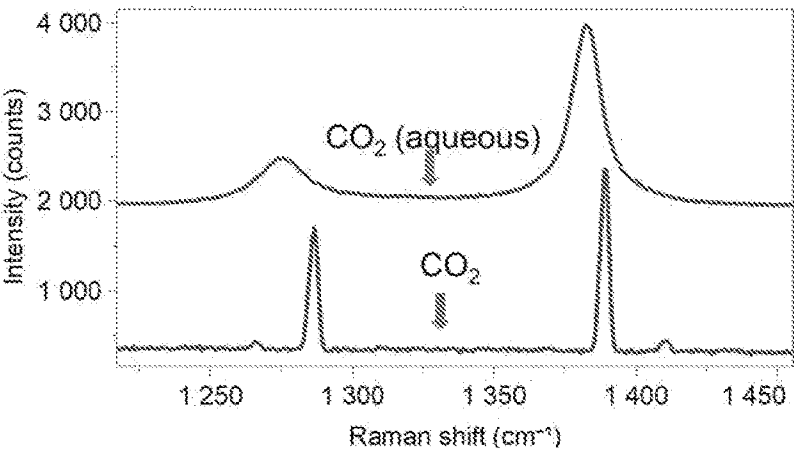
FIG. 4 depicts Fermi diads of $CO_2$ gas (99.8%, bottom line) and aqueous or dissolved $CO_2$ gas (99.8%, top line).

An ab initio study of $CO_2$ in aqueous solution was done by Sato et al.[9] to compute the solvation effect on the dipole moment and geometry of $CO_2$. As per this study $CO_2$ does not appear to have a net dipole moment in the presence or the absence of water molecules. The bond length of $CO_2$ (of C═O in $CO_2$) in the gaseous and the aqueous state was calculated to be 1.176 Å and 1.177 Å, respectively. The small change in the $CO_2$ molecule bond length is consistent with the small change in the Fermi diad position of $CO_2$ upon solvation (FIGS. 3 and 4).

High Pressure Raman Cell

Figure 5:
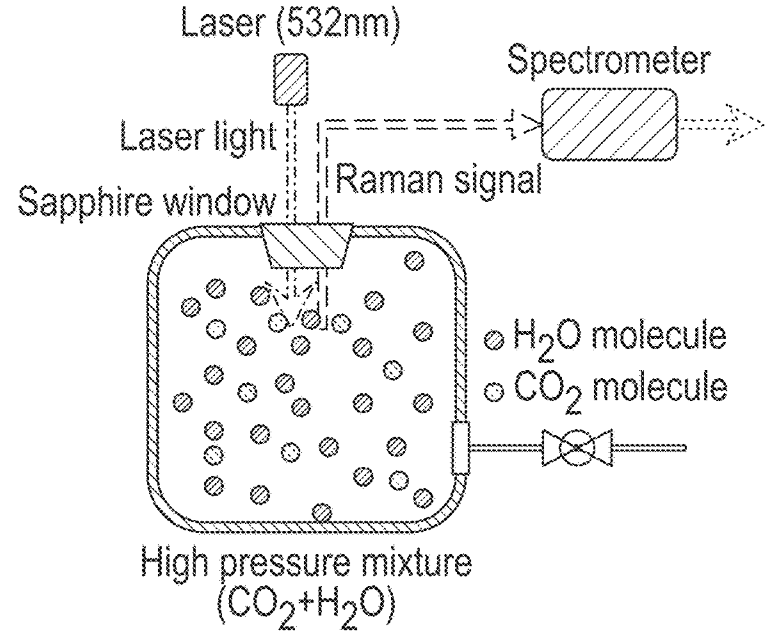
FIG. 5 depicts a schematic of an illustrated sample cell configured to acquire Raman spectra of a fluid that includes a gas dissolved in a liquid, according to one or more embodiments described.
Figure 6:
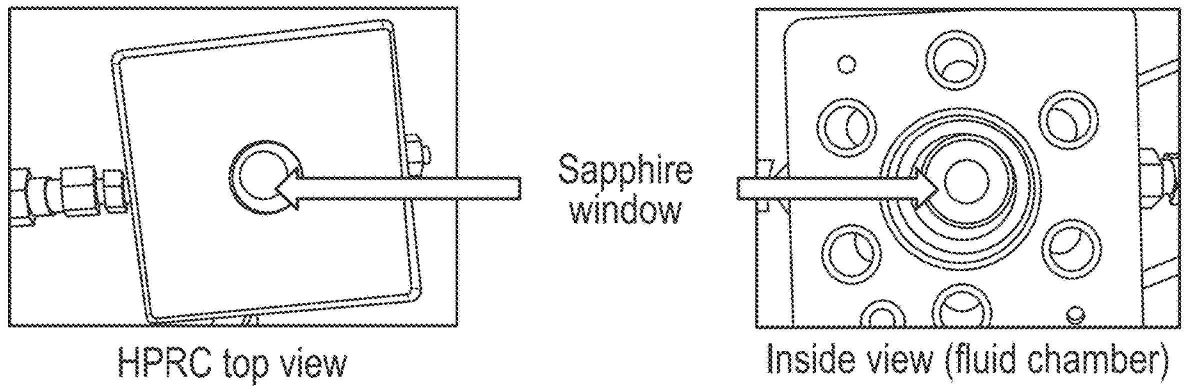
FIG. 6 depicts a top view and an inside view of the sample cell shown in FIG. 4, according to one or more embodiments described.
Figure 7:
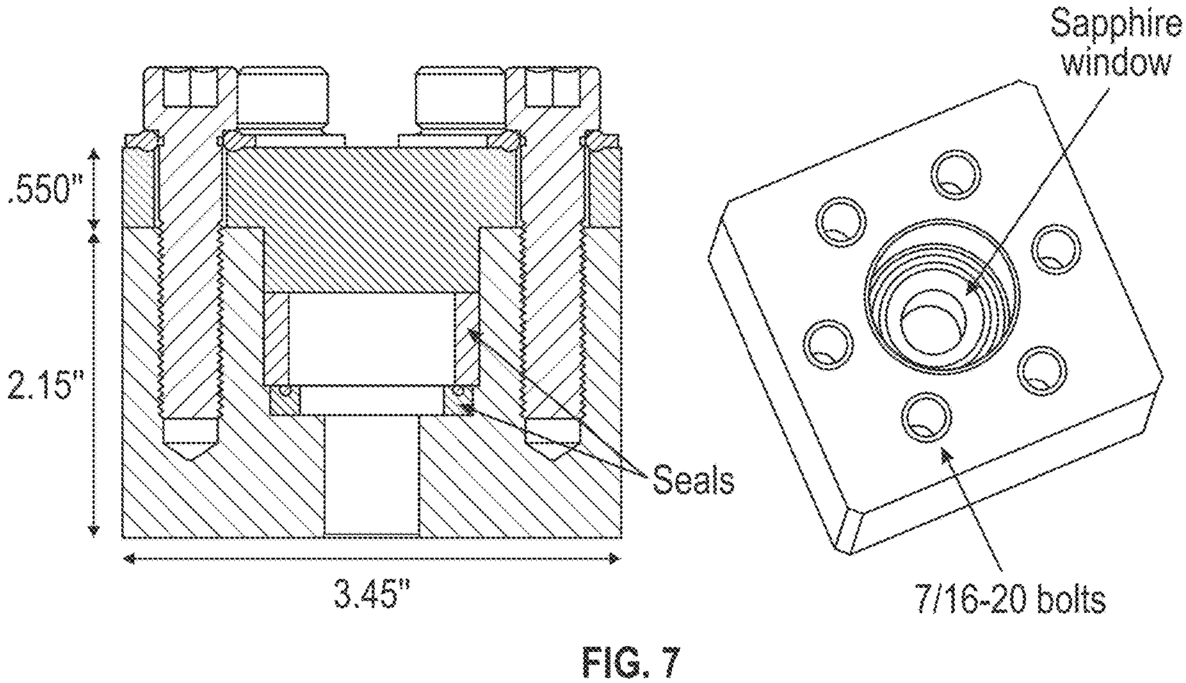
FIG. 7 depicts a cross sectional view and another inside view of the sample cell, according to one or more embodiments described.

A high-pressure optical cell for in situ Raman measurements of gases dissolved in liquid has been developed. FIG. 5 depicts a schematic an experimental setup of the high pressure Raman cell (HPRC) configured to acquire the Raman spectra of a $CO_2$—$H_2O$ mixture. Photographic images of the HPRC are shown in FIG. 6. This system can be directly plugged into any pressurized flow line of a surface processing facility or a downhole sampling station. Conventional high-pressure optical cells can only observe a single sample under elevated pressure. The HPRC disclosed herein can be integrated into a flowline for continuous monitoring. By changing the window configuration of the proposed design, we can modify the cell for transmission or absorption based measurements. The HPRC can be constructed of any suitable material, e.g., a stainless steel alloy, that can be rated to a desired pressure, e.g., at least 200 bar. The HPRC can be approximately cube-shaped and can have of lineal dimensions of about 8.9 cm. The sample compartment within the HPRC can have any desired volume, e.g., about 11 $cm^3$. The optical window can be made out of any desired material. In some embodiments, the optical windows can be made of sapphire (single-crystal $Al_2O_3$), quartz ($SiO_2$), or magnesium fluoride ($MgF_2$). The particular type of window can be based, at least in part, on the specific application and measurement(s) to be acquired. The thickness of the optical window can be sufficient to provide the optical window with the ability to withstand expected pressures within the HPRC. In some embodiments, the optical window can have a thickness of about 1.5 cm, about 2 cm, or about 2.5 cm to about 3 cm, about 3.5 cm, or about 4 cm such as about 2.54 cm. The optical window can be pressure sealed between two parts of the HPRC using a rubber seal, polytetrafluoroethylene, a gold O-ring, or the like. The mechanical construction of the HPRC is shown in FIG. 7. It should be understood that the dimensions shown in FIG. 7 are of only a single embodiment and any desired dimensions can be used in the manufacture of the HPRC.

The HPRC can be used with several commercial Raman instruments. In work discussed herein, the Raman spectra was collected using a micro-spectrometer Raman Horiba Jobin Yvon LabRAM Aramis. In this spectrometer, the electromagnetic radiation signal (monochromatic laser light of 532 nm) was passed through an optical assembly, which included a set of aligned mirrors, beam splitter, slits, and lenses. This light was emitted into the sample cell through the optical window. It should be understood that the electromagnetic radiation signal can have any desired wavelength. In some embodiments, the electromagnetic radiation signal can have a wavelength in the visible spectrum of about 400 nm to ≤700 nm, in the near infrared spectrum having a wavelength of >700 nm to about 1,400 nm or >700 nm to about 1,064 nm or in the near ultraviolet spectrum having a wavelength of about 300 nm to <400 nm. The scattered light from the sample was directed through notch filters, a grating, and onto a multi-channel charge-coupled device (CCD) detector. Notch filters in the optical path removed the large contribution of Rayleigh scattering from the signal. In some embodiments, the filter can be or can include, but is not limited to, one or more notch filters, one or more edge pass filters, one or more band pass filters, or a combination thereof. The grating included 1800 groves per mm and was used to disperse the incoming Raman and sort the incoming polychromatic light into monochromatic components. In some embodiments, the grating can have about 300 grooves/mm, about 600 grooves/mm, about 900 grooves/mm about 1,200 grooves/mm, about 1,600 grooves/mm, or about 1,800 grooves/mm to 2,000 grooves/mm, 2,400 grooves/mm, 2,800 grooves/mm, 3,200 grooves/mm or about 3,600. The CCD detector was a 2D array of light sensitive elements that interacted with the monochromatic components to build up charge to record the Raman signal.

Calibration and Experiments

The calibration of Raman spectra for $CO_2$ sensing was based on correlating the Raman signal to the dissolved $CO_2$ concentration. For this, a high-pressure equilibrated $CO_2$-water mixture was prepared. It was important to ensure thermodynamic equilibrium of the mixture so that the concentration of $CO_2$ in the gas or liquid phase of the $CO_2$-water mixture could be accurately estimated. As defined in U.S. Pat. No. 9,500,583B2, which is incorporated by reference, dissolved carbon dioxide is described as in thermodynamic equilibrium as long as the headspace is allowed to be present at the measured pressure and temperature if one knows the vapor pressure of water (or neglects it, if it is small). A $CO_2$ backpressure regulated bubbling device through an aqueous column was built to prepare the mixture. After prolonged bubbling, the equilibrated $CO_2$-water mixture was introduced into the HPRC. Degassing in the flowline was avoided by elevating the pressure slightly post equilibrium, and then flowing the solution to the measurement chamber. The absence of gas phase $CO_2$ was confirmed by analyzing the acquired Raman spectra for features specific to gaseous $CO_2$.

Figure 8:
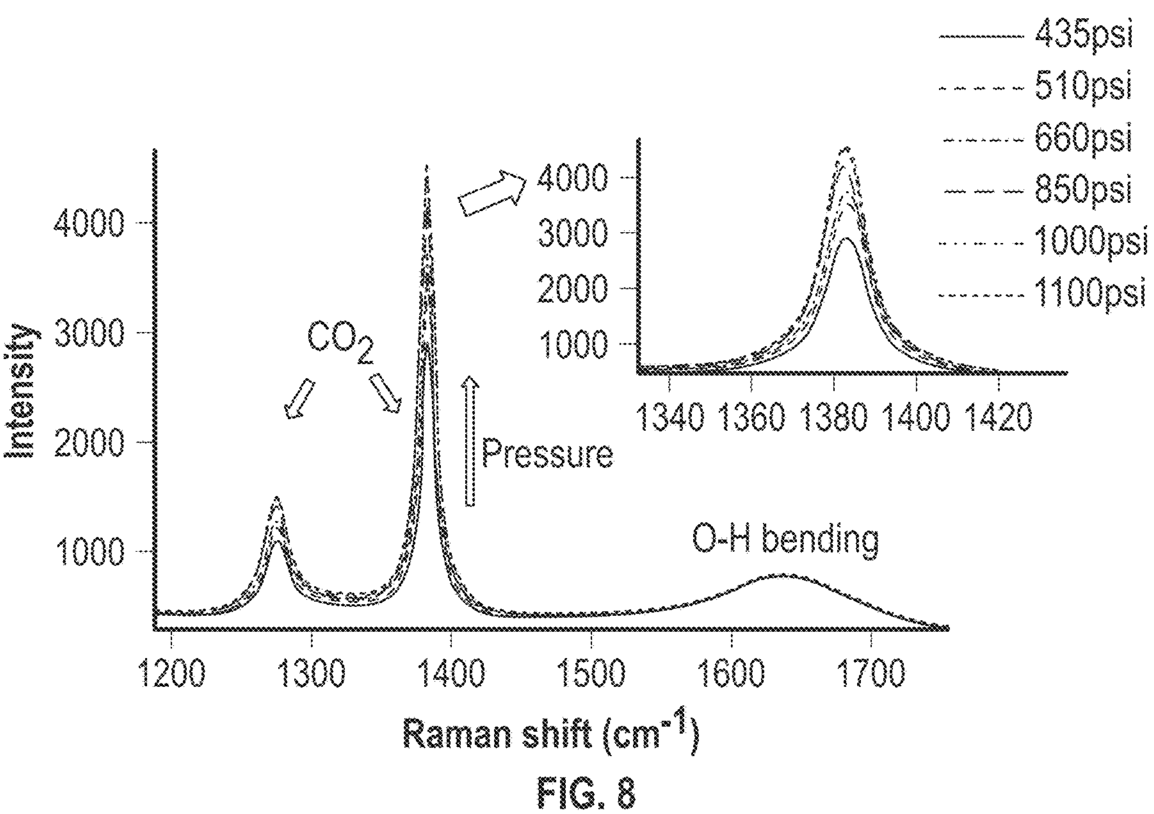
FIG. 8 depicts spectral shift data for a sample of $CO_2$ dissolved in water acquired at different pressures.

The Raman spectral data was acquired for a wide range of pressures, 435 psi-absolute to 1,100 psi-absolute, as shown in FIG. 8. In some embodiments, the Raman spectra data can be acquired from a fluid that includes the gas dissolved in the liquid that can be at a pressure of about 14.7 psi-absolute, about 50 psi-absolute, about 100 psi-absolute, about 200 psi-absolute, about 300 psi-absolute, about 400 psi-absolute or about 500 psi-absolute to about 660 psi-absolute, about 850 psi-absolute about 1,000 psi-absolute, about 1,100 psi-absolute, about 1,500 psi-absolute, about 1.750 psi-absolute, or about 2,000 psi-absolute. In some embodiments, the fluid can be at a pressure of ≥14.7 psi-absolute, ≥50 psi-absolute, ≥100 psi-absolute, ≥200 psi-absolute, ≥300 psi-absolute, ≥400 psi-absolute, ≥435 psi, ≥510 psi, ≥660 psi, ≥850 psi, ≥1,000 psi, or ≥1,100 psi.

The spectral region displayed highlights the Fermi diads of dissolved $CO_2$ and the water molecule (OH bend) features. The peak intensity of $CO_2$ increased as the pressure of the mixture increased. The experiments confirmed that reliable $CO_{2(liq)}$ sensing can be achieved by tracking the Fermi diad feature at 1383 $cm^{-1}$ as the $CO_2$ signature, and the OH spectral peak (1500-1800 $cm^{-1}$) as the $H_2O$ signature. The temperature for all measurements was 22° C.

Figure 9:
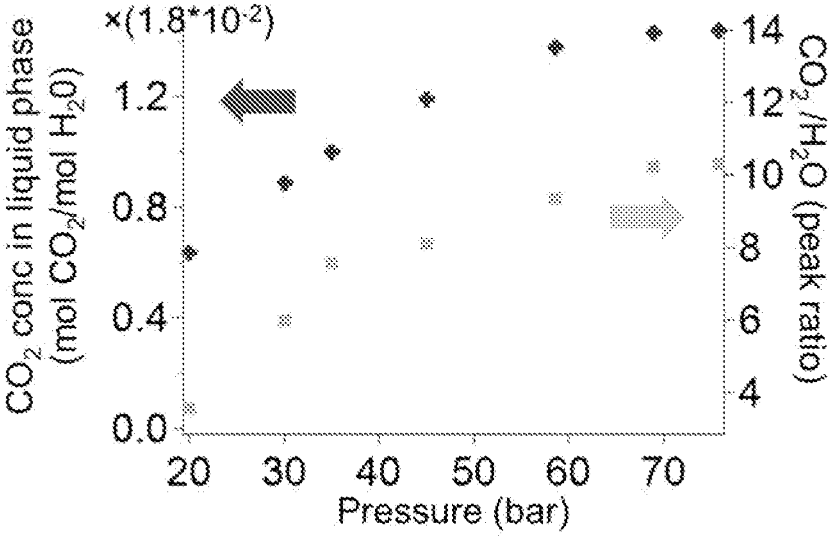
FIG. 9 depicts an illustrative calibration plot for a sample of $CO_2$ dissolved in water at different pressures.
Figure 10:
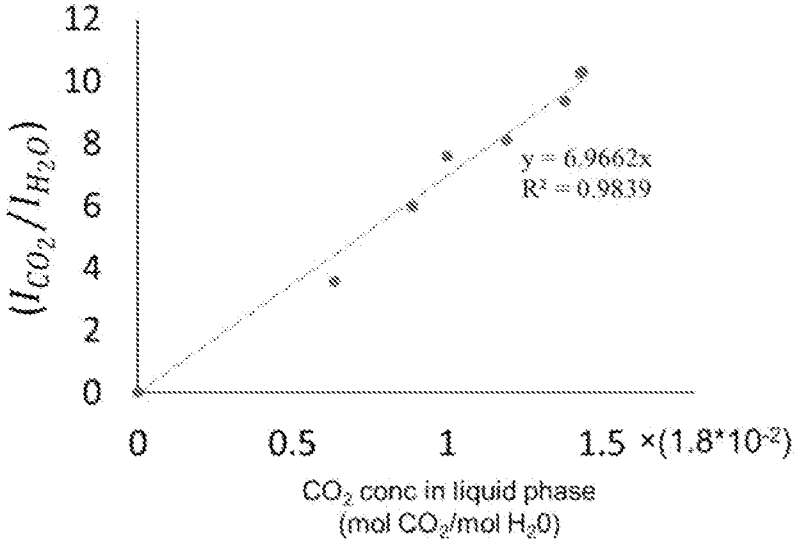
FIG. 10 depicts a calibration correlation for a molar ratio of $CO_2$ to water in the sample used to generate the calibration plot shown in FIG. 8.

Since the $CO_2$ and water mixture was at thermodynamic equilibrium, the Duan $CO_2$—$H_2O$ model can be applied and the liquid phase compositions can be calculated.[10, 11] FIG. 9 shows plots of the Raman and thermodynamic concentration (conc) data at different pressures (P). Each data point represents a new experiment. Concentration vs P in blue (top curve) was the predicted $CO_2$ concentration based on the Duan model. The plot in green (bottom curve) is the Raman intensity ratio ($I_{CO_2}/I_{H_2O}$) vs P. As shown in the two plots in FIG. 9, (i) conc versus P in blue (top curve) and (ii) ($I_{CO_2}/I_{H_2O}$) versus P in green (bottom curve), showed a similar qualitative trend with pressure. These two plots can be used to generate a calibration cross-plot, as shown in FIG. 10. A strong positive correlation between $I_{CO_2}/I_{H_2O}$ and the concentration for the pressure range of 0 bar to 75 bar was observed. Note that the concentration is expressed as molar ratios of $CO_2$ and $H_2O$.

Use-Cases of Monitoring System

The utility and feasibility of field deployment of the HPRC system in aquifer and hydrocarbon reservoir CO2 injection projects were studied.

Figure 11:
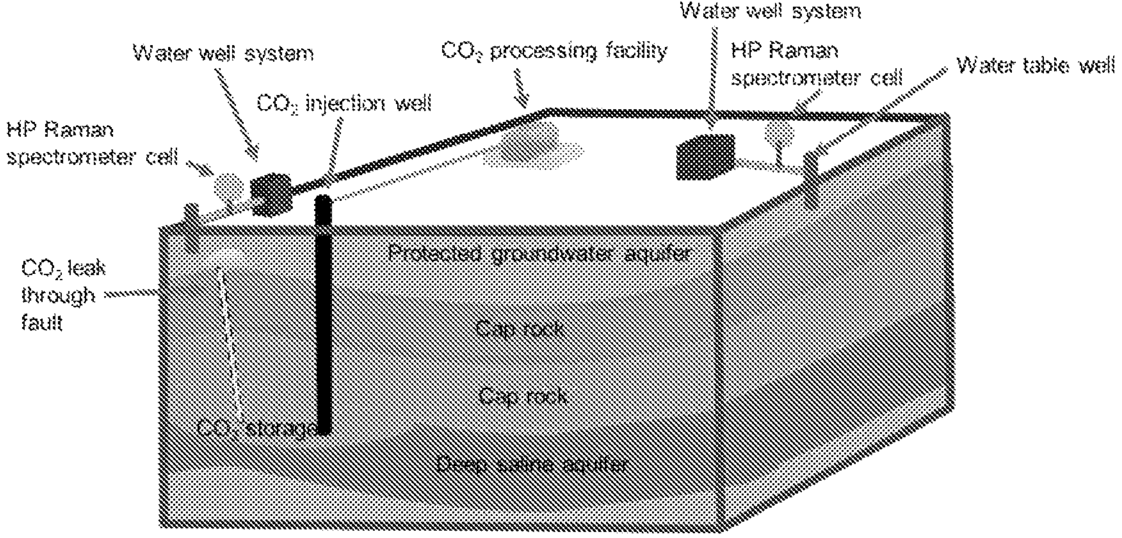
FIG. 11 depicts an illustrative system for monitoring $CO_2$ dissolved in water in a saline aquifer being used to sequester $CO_2$, according to one or more embodiments described.

FIG. 11 depicts some locations where sensors can be deployed in a geological $CO_2$ sequestration in saline aquifer operation, according to one or more embodiments. The integrity of geological $CO_2$ sequestration can be monitored over an extended period of time (decades). Aquifers can enhance $CO_2$ storage potential through dissolution. Any upward migration of $CO_2$ can be inferred through changes in pressure, but a positive diagnosis of a leak can be obtained through a dissolved $CO_2$ measurement. As such a reliable monitoring process can be established to gather information about $CO_2$ concentration from samples collected from various depths of the reservoir (from surface to subsurface) along with their evolution. To detect migration pathways of $CO_2$, zoned sensing in monitoring wells can be carried out, especially if mitigation measures are also sought. The sensing system shown in FIG. 11, can be deployed in any well either between packed-off intervals or at the surface to monitor $CO_2$ leaks into the protected groundwater aquifer. Early detection of leakage of $CO_2$ into the groundwater or to the atmosphere can be used to prevent further undesirable migration by analyzing the data and identifying leakage pathways. More often than not the pathways caused by lack of wellbore integrity if so identified can be remedied fairly easily.

Figure 12:
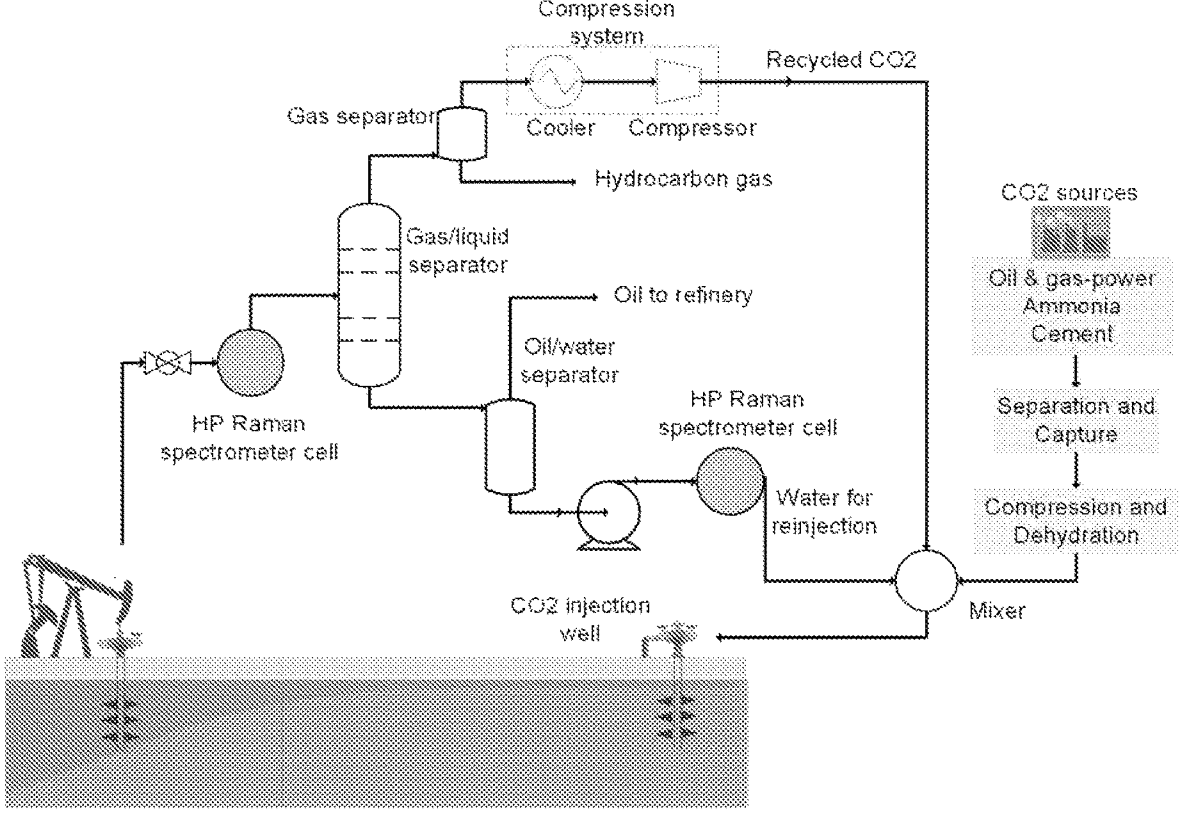
FIG. 12 depicts an illustrative system for monitoring $CO_2$ dissolved in water in a $CO_2$ enhanced oil recovery (EOR) facility, according to one or more embodiments described.

FIG. 12 depicts some locations where sensors can be deployed in a $CO_2$ enhanced oil recovery facility, according to one or more embodiments. It has been well established that $CO_2$ injection can improve the efficiency of oil recovery, with field experiments dating back almost 50 years.[12-18] Martin et al.[12] and Holm et al.[13] reported the early experimental studies on oil recovery with carbonated water. The first field demonstration was completed in 1972 at the SACROC (Scurry Area Canyon Reef Operators Committee) Unit. Several reservoir models are now available to determine the incremental oil recovery factors during the $CO_2$-EOR process at the level of an individual reservoir.[19] Similar to the first example in the $CO_2$-EOR application, it can be desirable that the non-recycled $CO_2$ be stored permanently in the reservoir within the pore spaces that were once occupied by the oil and water, or by dissolution in the oil and water remaining in the reservoir after the recovery process. The injected gas can be retained in the reservoir via one or more of structural, residual, dissolution, and mineral storage mechanisms. The monitoring of dissolved $CO_2$ in the production stream can be desirable since it can allow one to adjust operating points of recycling and cessation. Such a system can facilitate fine-grained sensing to check $CO_2$ retention rates within the reservoir during the EOR process as well as exit rates at surface facilities (e.g., gas-liquid separation system).

The sensing system can be adapted to meet the monitoring needs and can be deployed in multiple critical stages as shown in FIG. 12. In one embodiment, the sensing system can be used to monitor $CO_2$ concentration in the pressured flow line of the pumped hydrocarbon mixture before it is fed to the gas/liquid separator unit. In another embodiment, the sensing system can be deployed to monitor the $CO_2$ concentration in water discharged from the oil/water separator unit for further disposal decisions. In some embodiments, the sensing system can be installed semi-permanently downhole for zonal $CO_2$ monitoring that can be used to infer contact factor.

Raman-based monitoring can be tuned for downhole implementation depending on the spectrometer assembly. For surface monitoring a portable Raman spectrometer can be coupled to an existing well completion system for monitoring gas concentrations. This capability extends to produced oil with the exception of dissolved $CH_4$. One advantage of Raman spectroscopy is that once the sensing system has been calibrated, the sensing system is not affected by liquid or gas phase water.

In some embodiments, information on the one or more gases dissolved in the liquid can be used to help (i) make operational decisions in a $CO_2$ enhanced oil recovery operation, e.g., optimization of a surface facility operating conditions for separation, compression, and reinjection, (ii) develop a corrosion mitigation plan upon detection of acidic gases, and/or (iii) assign value to produced hydrocarbons.

In the context of a $CO_2$ enhanced oil recovery operation, a robust composition sensor for both dense and light phases in the production string can be useful. For design purposes, the hydrocarbon composition at the end of a secondary flood can be useful. The terminal portion of the secondary flood can be regarded as the preparatory design phase for tertiary recovery. During this phase, downhole fluid analyzers can provide component fractions for flexible surface facility design for which IR transmission measurements alone are insufficient. Continuous update to optimization can be benefitted by online compositional analysis. In $CO_2$ enhanced oil recovery, the fraction of $CO_2$ in the produced hydrocarbon increases. With progress in production, at some point, separation and reinjection can become uneconomical. More importantly, this may not be universal within a well, and may vary with completed zones. Under these circumstances, particularly in commingled production, downhole zonal compositional data can be useful. The Raman spectroscopy based sensing system can be used for obtaining these data.

In the context of corrosion mitigation planning, it is well known that high concentrations of $CO_2$ in the presence of moisture accelerates corrosion of critical elements such as casing strings, tubing, and pipelines. Furthermore, it can be desirable to detect and quantify the evolution of $H_2S$ on a continuous manner to ensure the material integrity and operational safety. Any separated $H_2S$ may need to be reinjected to another contained stratum that has its own constraints. Thus, reliable and simultaneous monitoring of $CO_2$ and other corrosive gases in the oilfield can be beneficial.

Although the preceding description has been described herein with reference to particular means, materials, and embodiments, it is not intended to be limited to the particulars disclosed herein; rather, it extends to all functionally equivalent structures, processes, and uses, such as are within the scope of the appended claims.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value. As used herein the terms "about" and "approximately" are used interchangeably, and refer to any experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application, including references 1-22 listed above, are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for sensing a gas dissolved in a liquid, comprising:

calibrating a sample cell for sensing the gas dissolved in the liquid comprising preparing a mixture comprising water and at least one gas at a pressure of about 14.7 psi-absolute to about 2,000 psi-absolute, wherein the at least one gas is dissolved in the water, and wherein the mixture is at thermodynamic equilibrium;

introducing a fluid into an inlet of the sample cell, wherein the fluid comprises at least one gas dissolved in at least one liquid;

flowing the fluid through the sample cell, wherein at least a portion of the fluid flows past an optical window such that the fluid is viewable within the sample cell through the optical window;

recovering the fluid from an outlet of the sample cell;

emitting an electromagnetic radiation signal into the sample cell through the optical window for at least a portion of the time the fluid is viewable through the optical window;

contacting the fluid with the electromagnetic radiation signal within the sample cell;

directing a scattered electromagnetic radiation signal comprising Rayleigh scattering and Raman scattering emitted from the sample cell through the optical window into a filter to remove at least a portion of the Rayleigh scattering to produce a primarily Raman scattering signal; and directing the primarily Raman scattering signal to a detector to detect a Raman signal indicating the presence of the at least one gas dissolved in the at least one liquid at a pressure ranging from about 435 psi-absolute to about 1,100 psi-absolute.

2. The process of claim 1, wherein a wavelength of the electromagnetic radiation signal is in the visible spectrum having a wavelength of about 400 nm to ≤700 nm, in the near infrared spectrum having a wavelength of >700 nm to about 1,400 nm, or in the near ultraviolet spectrum having a wavelength of about 300 nm to <400 nm.

3. The process of claim 1, wherein the filter comprises a notch filter, an edge pass filter, a band pass filter, or any combination thereof.

4. The process of claim 1, further comprising directing the primarily Raman scattering signal through a grating to separate the primarily Raman scattering signal into monochromatic components, such that the monochromatic components are directed to the detector.

5. The process of claim 4, wherein the grating comprises about 300 grooves to about 3,600 grooves per mm.

6. The process of claim 1, further comprising passing the electromagnetic radiation signal through an optical assembly prior to emitting the electromagnetic radiation signal into the sample cell through the optical window.

7. The process of claim 1, wherein the fluid is at a pressure of about 14.7 psi-absolute to about 2,000 psi-absolute.

8. The process of claim 1, wherein the fluid is at a pressure of greater than or equal to 14.7 psi-absolute, greater than or equal to 50 psi-absolute, greater than or equal to 100 psi-absolute, greater than or equal to 200 psi-absolute, greater than or equal to 300 psi-absolute, greater than or equal to 400 psi-absolute, greater than or equal to 435 psi, greater than or equal to 510 psi, greater than or equal to 660 psi, greater than or equal to 850 psi, greater than or equal to 1,000 psi, or greater than or equal to 1,100 psi.

9. The process of claim 1, wherein the fluid is introduced into the inlet and recovered from the outlet of the sample cell for continuous monitoring.

10. The process of claim 9, wherein the electromagnetic radiation signal is emitted into the sample cell through the optical window for continuous monitoring, such that the primarily Raman scattering signal is directed to the detector to detect the Raman signal indicating the presence of the at least one gas dissolved in the at least one liquid by flowing the at least one liquid through a flowline and into the inlet of the sample cell.

11. The process of claim 9, wherein the electromagnetic radiation signal is emitted into the sample cell on a periodic basis, such that the primarily Raman scattering signal is directed to the detector to detect the Raman signal indicating the presence of the at least one gas dissolved in the at least one liquid in one or more separate samples.

12. The process of claim 1, wherein the at least one gas dissolved in the at least one liquid comprises $CO_2$, $CH_4$, $H_2S$, $N_2$, or any mixture thereof.

13. The process of claim 1, wherein the at least one liquid comprises water or a hydrocarbon oil.

14. The process of claim 1, wherein the optical window comprises $Al_2O_3$, $SiO_2$, or $MgF_2$.

15. The process of claim 1, further comprising:

obtaining a hydrocarbon production fluid from a hydrocarbon well, wherein the fluid comprises the hydrocarbon production fluid.

16. The process of claim 1, further comprising:

obtaining a hydrocarbon production fluid from a hydrocarbon well;

monitoring a $CO_2$ concentration of the hydrocarbon production fluid in a pressured flow line before the hydrocarbon production fluid is fed into a gas/liquid separator unit to produce a gas phase product and a liquid phase product; and monitoring a $CO_2$ concentration of an aqueous product produced by introducing the liquid phase product into an oil/water separator unit to produce a hydrocarbon product and the aqueous product, wherein the fluid comprises the aqueous product.

17. The process of claim 1, further comprising sensing the presence of one or more additional gases dissolved in the at least one liquid with a transmission infrared measurement system.

18. The process of claim 17, wherein the one or more additional gases sensed by the transmission infrared measurement system comprises $CO_2$, $CH_4$, $H_2S$, or any mixture thereof.

19. A process for calibrating a Raman system, comprising:

preparing a mixture comprising water and at least one gas at a pressure of about 14.7 psi-absolute to about 2,000 psi-absolute, wherein the at least one gas is dissolved in the water, and wherein the mixture is at thermodynamic equilibrium;

flowing the mixture through a flowline and into an inlet of a sample cell, wherein degassing in the flowline is substantially avoided by increasing the pressure by at least 1 psi-absolute above the pressure the mixture of water and the at least one gas was prepared;

flowing the mixture through the sample cell, wherein at least a portion of the mixture flows past an optical window such that the mixture is viewable within the sample cell through the optical window;

recovering the mixture from an outlet of the sample cell;

emitting an electromagnetic radiation signal into the sample cell through the optical window for at least a portion of the time the mixture is viewable through the optical window;

contacting the mixture with the electromagnetic radiation signal within the sample cell;

directing a scattered electromagnetic radiation signal comprising Rayleigh scattering and Raman scattering emitted from the sample cell through the optical window into a filter to remove at least a portion of the Rayleigh scattering to produce a primarily Raman scattering signal;

directing the primarily Raman scattering signal to a detector to detect a Raman signal indicating the presence of the at least one gas dissolved in the water; and correlating the Raman signal to a dissolved concentration of the at least one gas with a thermodynamic model for the mixture of water and the at least one gas.

20. The process of claim 19, wherein the at least one gas comprises $CO_2$, $CH_4$, $H_2S$, $N_2$, or any mixture thereof.

21. The process of claim 19, wherein the mixture consists essentially of water and the at least one gas.

22. The process of claim 19, wherein degassing in the flowline is substantially avoided by increasing the pressure by at least 3 psi-absolute, at least 5 psi-absolute, at least 10 psi-absolute, at least 15 psi-absolute, at least 20 psi-absolute, or at least 25 psi-absolute above the pressure the mixture of water and the at least one gas was prepared.

23. The process of claim 19, wherein the process is repeated for a plurality of mixtures, wherein each mixture of the plurality of mixtures is prepared at a different pressure to produce a calibration curve showing a concentration of the at least one gas dissolved in the water for each mixture in the plurality of mixtures prepared at the different pressures.

24. The process of claim 19, wherein a wavelength of the electromagnetic radiation signal is in the visible spectrum having a wavelength of about 400 nm to ≤700 nm, in the near infrared spectrum having a wavelength of >700 nm to about 1,400 nm, or in the near ultraviolet spectrum having a wavelength of about 300 nm to <400 nm.

25. The process of claim 19, wherein the filter comprises a notch filter, an edge pass filter, a band pass filter, or any combination thereof.

26. The process of claim 19, further comprising directing the primarily Raman scattering signal through a grating to separate the primarily Raman scattering signal into monochromatic components, such that the monochromatic components are directed to the detector.

27. The process of claim 26, wherein the grating comprises about 300 grooves to about 3,600 grooves per mm.

28. The process of claim 19, further comprising passing the electromagnetic radiation signal through an optical assembly prior to emitting the electromagnetic radiation signal into the sample cell through the optical window.

* * * * *